United States Patent [19]
Peckham et al.

[11] Patent Number: 5,569,286
[45] Date of Patent: Oct. 29, 1996

[54] LANCET ASSEMBLY

[75] Inventors: Allison A. Peckham, Pompton Plains, N.J.; Lennox O. Watts, Bronx; Marina Gertsek, Manhattan County, both of N.Y.; Kevin R. Smith, Holdrege, Nebr.; Don D. Taubenheim, Holdrege, Nebr.; Ronald J. Pistulka, Holdrege, Nebr.

[73] Assignee: Becton Dickinson and Company, Franklin Lakes, N.J.

[21] Appl. No.: 413,044

[22] Filed: Mar. 29, 1995

[51] Int. Cl.$^6$ ............................................ A61B 17/14
[52] U.S. Cl. .................. 606/181; 606/182; 606/185; 604/192; 604/198
[58] Field of Search ................................ 606/181, 185, 606/182; 604/198, 192, 263; 30/340, 342

[56] References Cited

U.S. PATENT DOCUMENTS

| | | | |
|---|---|---|---|
| 4,580,564 | 4/1986 | Andersen | 606/181 |
| 5,324,303 | 6/1994 | Strong et al. | 606/181 |
| 5,385,571 | 1/1995 | Morita | 606/181 |
| 5,454,828 | 10/1995 | Schraga | 606/181 |

*Primary Examiner*—Michael Powell Buiz
*Assistant Examiner*—Kevin Truong
*Attorney, Agent, or Firm*—Alan W. Fiedler

[57] ABSTRACT

A lancet assembly includes an injection molded housing with a metal stylet mounted therein and a cap or shield. The stylet is held in position by adhesive and a plurality of supports that retain a centrally located hub within a lower portion of the housing. An improved cap is provided for mounting over the stylet on the lower portion of the housing to shield the stylet prior to use. The cap also includes an octagonal flange at its lower end to ease removal of the cap from the housing and to provide a flat octagonal surface for independent standing during reshielding. The housing of the lancet assembly includes a plurality of molded-in longitudinal splines that provide a textured surface on the exterior of the housing to make the housing easier to handle and manipulate when loading the lancet assembly into a blood sampling instrument and includes an annular flange extending from the exterior surface of the housing to make insertion/removal of shielded lancet assembly into/from a blood sampling instrument easier.

13 Claims, 5 Drawing Sheets

LANCET ASSEMBLY

BACKGROUND OF THE INVENTION

1. Field of the Invention

The present invention relates to a lancet assembly and, more particularly, to a lancet assembly having an injection molded housing with a metal stylet mounted therein and an injection molded removable cap or shield over the housing to protect the stylet.

2. Background Description

A lancet is a device commonly used in hospitals, doctors offices and homes to pierce a patient's flesh to draw capillary blood for diagnostic testing. Conventional lancets consist of a shank portion having at a distal end a blade or spike, which is sharp and adapted to pierce the patient's skin so to sever capillaries and provide blood for testing. Since the blade or spike is sharp, some lancets are provided with a removable shield for protectively covering the sharp edge or point of the lancet's blade or spike when not in use to protect the patient and users from inadvertent skin puncture.

There are a number of conventional lancet instruments available to aid a user in puncturing or penetrating a patient's skin to draw and sample a small outflow of blood. For example, U.S. Pat. No. 4,577,630 (Nitzsche et al), which is assigned to Becton, Dickinson and Company, shows a disposable lancet assembly for use in a reusable breach loading target pressure activated lancet firing device. The lancet assembly includes a rectangular handle portion, a lancet point extending outwardly from a distal end of the handle portion, and a removable shield adapted to mate with the lancet point when the lancet assembly is not in use to protect users from accidental puncture.

U.S. Pat. No. 4,517,978 (Levin et al.) shows another type of blood sampling instrument for drawing a blood sample from a patient's finger. The instrument described in Levin et al. includes a reusable tubular housing having a spring chamber for driving a needle held in a disposable needle holder into a patient's finger, when a trigger button on the side of the tubular housing is depressed. Prior to use, a disposable needle holder is slidably mounted in a socket within the tubular housing on a plunger member and the plunger member is slid to an armed position. The armed instrument is then placed against a patient's finger and activated using the trigger button. When activated the instrument drives the plunger towards the distal end of the instrument which causes the needle in the disposable needle holder on the plunger to pierce the patient's skin and create a drop of blood sufficient for testing.

As suggested by Levin et al., in Col. 2, lines 17-19, there are conventional disposable needle holders available on the market for use with the Levin et al. instrument, e.g., a MONOLET™ lancet assembly. However, conventional lancet assemblies are difficult to handle and manipulate when loading the instrument and have shields mounted directly on their needles that are difficult to remove from the needle and may cause damage to the needle when being removed. In addition, conventional needle holders are manufactured using insert molding, which is expensive and makes it difficult to inspect the assembly/needle and precisely place the needle within the needle holder to control penetration depth.

SUMMARY OF THE INVENTION

The present invention overcomes the problems identified in the background material by providing a disposable lancet assembly for use in a blood sampling instrument having an injection molded housing with a metal stylet, e.g., 28 gauge, mounted therein and an improved cap or shield with a flange for ease of removal.

The injection linear molded housing is circular in diameter and includes a circular, full circumference flange extending therefrom. Molded-in longitudinal splines form a surface on the exterior of the housing to make the housing easier to handle and manipulate when loading the lancet assembly into a blood sampling instrument. In addition, the housing is injection molded which makes it easier to inspect the stylet and permits the stylet to be precisely located and mounted within the housing with adhesive such that a predetermined length of the stylet protrudes from the distal end.

The improved cap or shield receives and mounts on the distal end of the housing and includes three labyrinth rings that form a labyrinth seal with the housing. The cap also includes an octagonal flange to ease removal of the cap from the housing prior to use and provide stability of the assembled lancet assembly when placed on a flat surface. The cap can also be placed on its flange end to allow re-shielding of the lancet assembly without holding the cap. In addition, the housing and cap are hollow to reduce the materials needed during manufacturing, improve manufacturability and reduce cost.

These and other aspects, features and advantages of the present invention will become apparent from the following detailed description taken in conjunction with the accompanying drawings.

DETAILED DESCRIPTION

Figure 1:
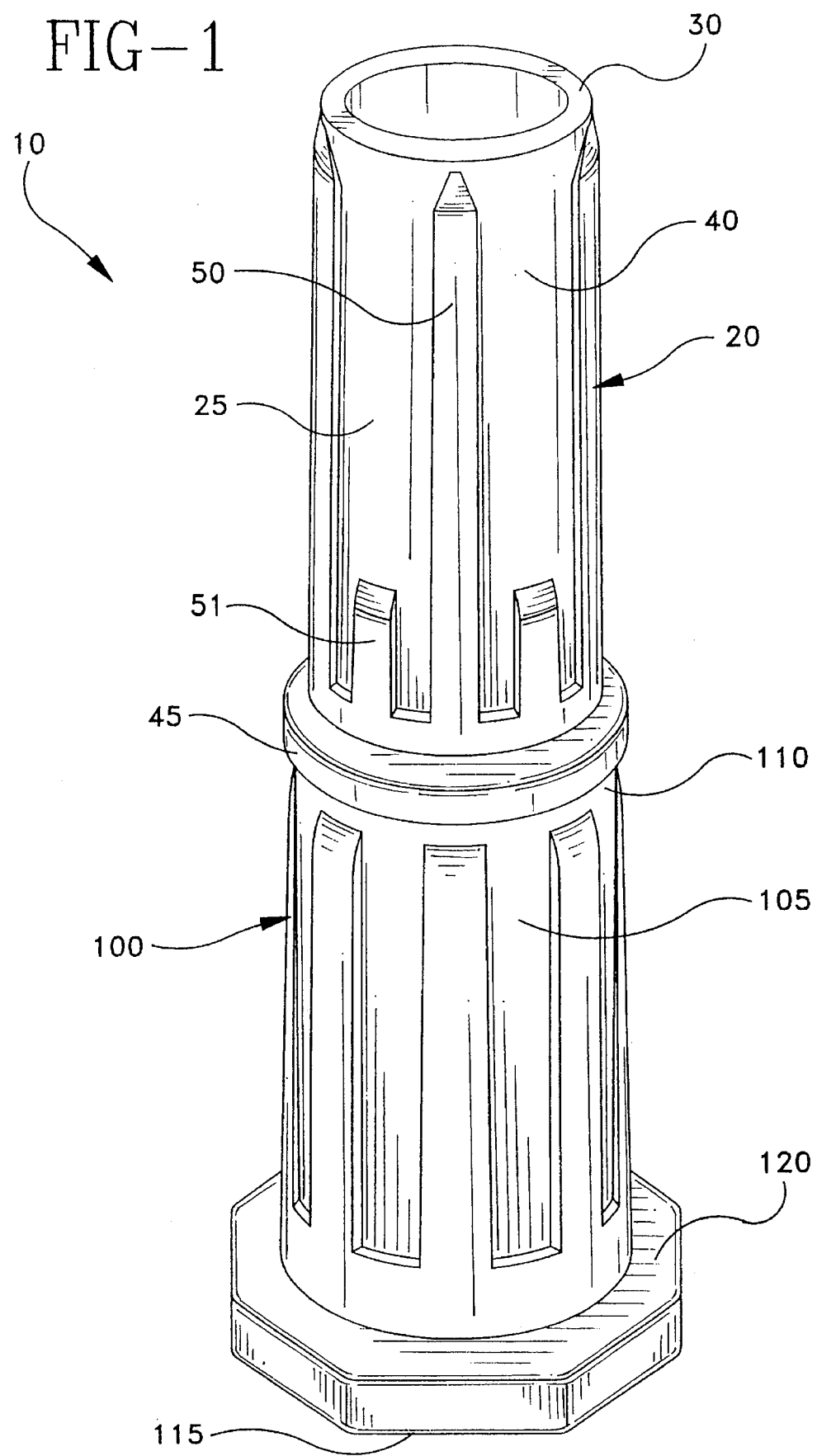
FIG. 1 is a perspective view of a shielded lancet assembly according to the present invention.

FIG. 1 is a perspective view of a shielded lancet assembly 10 according to the present invention for use in a blood sampling instrument similar to the one shown and described in U.S. Pat. No. 4.5 17,978 (Levin et al.), included herein by reference. Shielded lancet assembly 10 includes a lancet assembly 20 with a removable cap or shield 100 attached thereto to shield and protect a user from a stylet 55, shown in FIG. 2, in lancet assembly 20.

Figure 2:
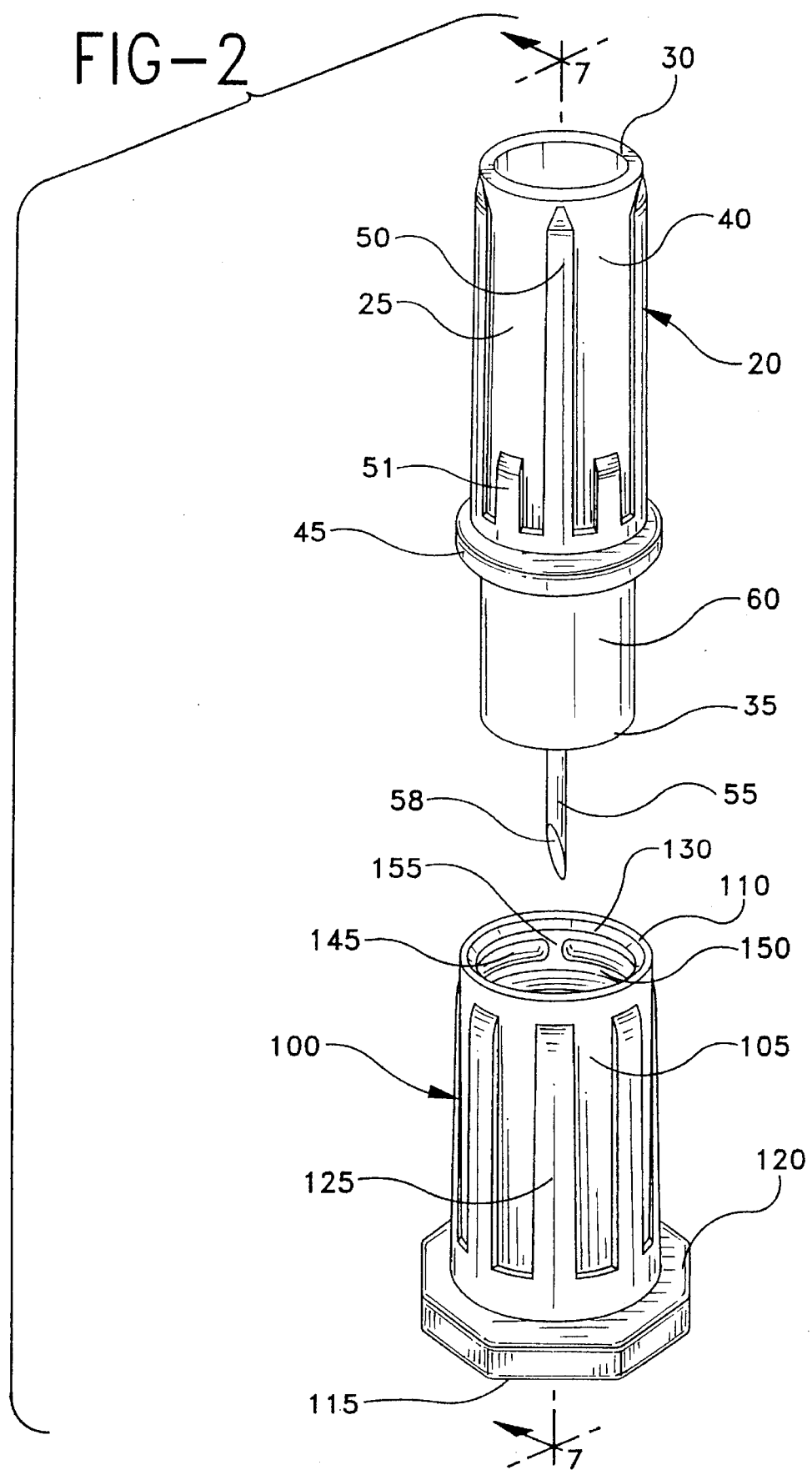
FIG. 2 is a perspective view of an unshielded lancet assembly according to the present invention.

Lancet assembly 20 includes a cylindrical housing 25 having a proximal top end 30 and a distal bottom end 35, shown in FIG. 2, connected by an outer wall 40. An annular flange 45 extends from outer wall 40 and surrounds housing 25. A plurality of longitudinal ribs or splines 50 and 51 on outer wall 40 extend frown flange 45 towards proximal end 30. Ribs 50 are longer than ribs 51 and alternate around outer wall 40 to provide a novel textured surface to improve handling, maneuverability and fit when lancet assembly 20 is mounted in a socket on the blood sampling instrument.

Removable cap 100 includes a cylindrical housing 105 having an open top end 110 and a closed bottom end 115. As shown in FIG. 2, distal bottom end 35 of lancet assembly 20 is received in open top end 110 of cap 100 to cover and shield stylet 55 mounted in distal end 35 of lancet assembly 20. Closed bottom end 115 on cap 100 includes an octagonal shaped flange 120 extending radially therefrom that improves the removability of cap 100 from lancet assembly 20 and handling of cap 100. Removable cap 100 also includes a plurality of longitudinal ribs or splines 125 on housing 105 that extend from octagonal shaped flange 120 toward open end 110. Ribs 125 provide a sufficient textured surface to improve handling and maneuverability of cap 100, when it is being removed from lancet assembly 20.

When lancet assembly 20 is used in the conventional Levin et al. blood sampling instrument, a shielded lancet assembly 10 is inserted in the socket in the distal end of the Levin et al. instrument. Cap 100 is then removed from lancet assembly 20 using octagonal shaped flange 120 to unshield stylet 55.

FIG. 2 is an exploded perspective view of an unshielded lancet assembly according to the present invention. A user removes cap 100 from distal bottom end 35 of lancet assembly 20 by applying a longitudinal force to octagonal shaped flange 120 sufficient to slide a lower annular portion 60 at the base of stylet 55 out of a chamber 130 in open top end 110 of cap 100. After the user has removed cap 100 from lancet assembly 20, the user positions the distal end of the Levin et al. instrument on the patient's finger and depresses the trigger button on the instrument. When the trigger button on the instrument is depressed, a spring chamber in the instrument drives stylet 55 into the patient's finger. FIG. 2 also shows a plurality of labyrinth rings 145 within cap 100, discussed below, and a sharpened point 58 on stylet 55. Preferably, stylet 55 is made of 28 gauge stainless steel. Conventional lancet stylets use larger gauge material. In addition, stylet 55 can be lubricated to reduce penetration force and thereby reduce pain to the patient during use. Of course, the above material and gauge are merely exemplary, other gauge materials could also be used in the present invention.

Figure 3:
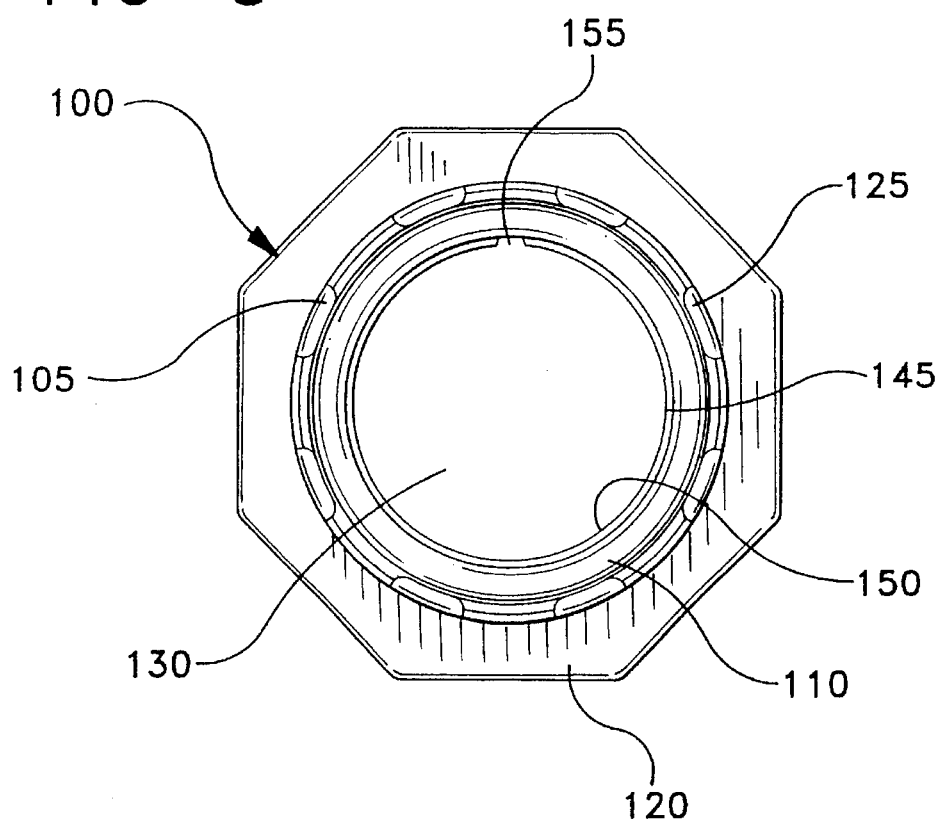
FIG. 3 is a top plan view of the cap shown in FIG. 2.
Figure 4:
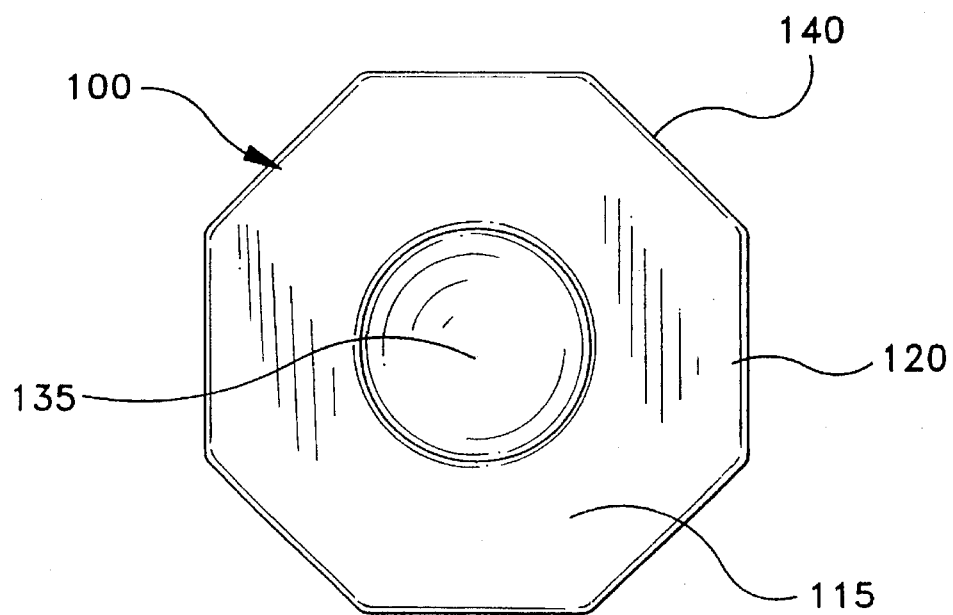
FIG. 4 is a bottom plan view of the cap shown in FIGS. 2 and 3.

FIG. 3 is a top plan view of cap or shield 100, shown in FIG. 2. As shown, cap 100 includes chamber 130 at its center surrounded by cylindrical housing 105. Three labyrinth rings 145, each provided with a gap 155 separated from ring to ring by 120 degrees, are provided around an interior wall 150 in housing 105 to provide sterility and a labyrinth seal between rings 145 and housing 25 when attached to lancet assembly 20. The interference fit between rings 145 and housing 25 also determine the removal force necessary to remove cap 100 frown lancet assembly 20. FIG. 3 also more clearly shows the positioning of ribs 125 around the circumference of housing 105 and the octagonal shape of flange 120. FIG. 4 is a bottom plan view of cap 100 and shows a concave circular center portion 135 in closed botton end 115. It should be appreciated that the octagonal shape of flange 120 provides a plurality of surfaces 140 that permit a user to more easily grasp cap 100 when removing it from lancet assembly 20. Octagonal shaped flange 120 also provides a flat resting surface to cause cap 100 to stand upright with open top end 110 up, thereby allowing for reshielding of lancet assembly 20 after use without the user holding cap 100.

Figure 5:
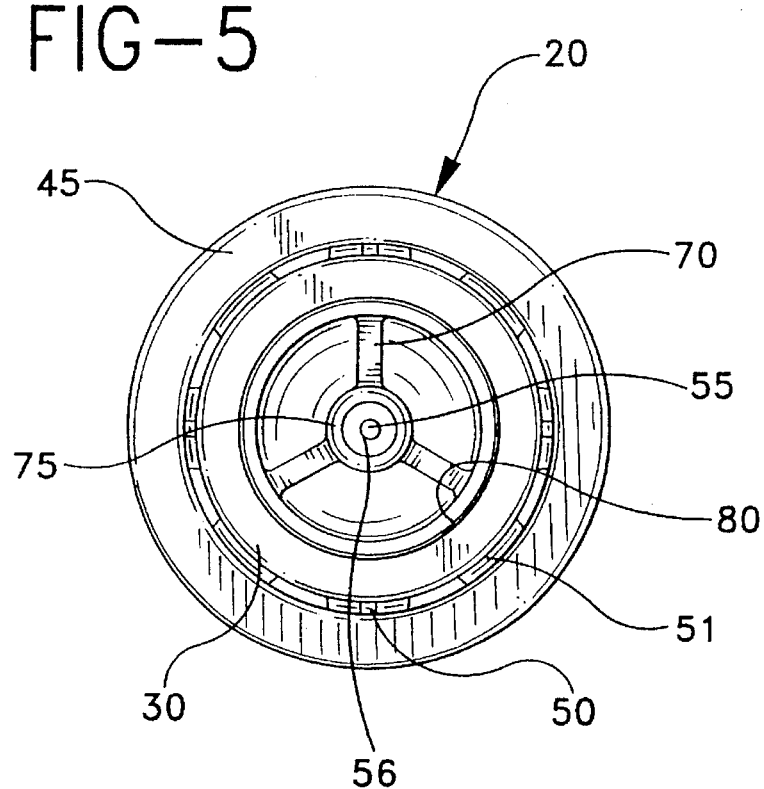
FIG. 5 is a top plan view of the lancet assembly shown in FIG. 2.
Figure 6:
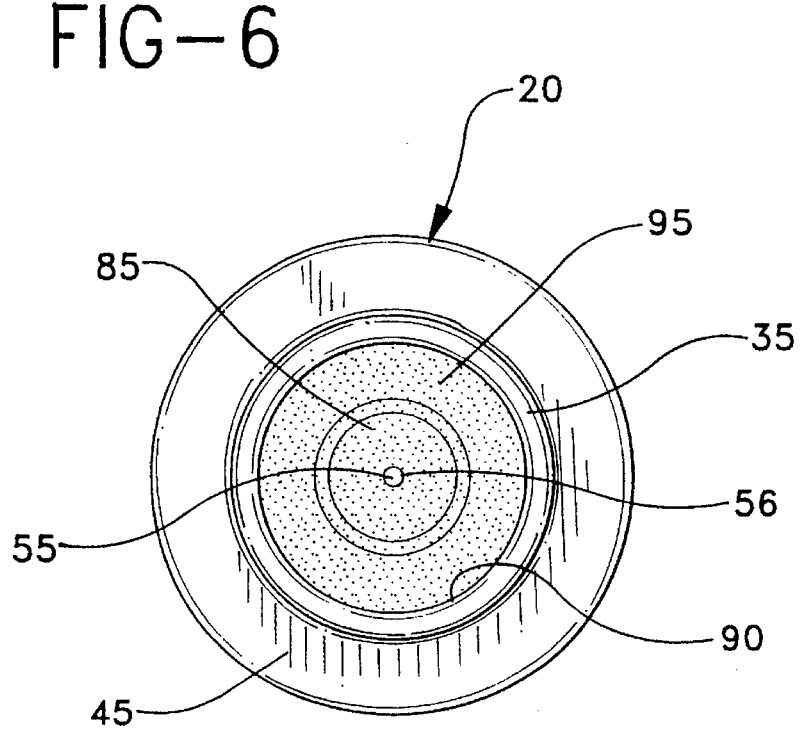
FIG. 6 is a bottom plan view of the lancet assembly shown in FIGS. 2 and 5.

FIG. 5 is a top plan view of lancet assembly 20 that more clearly shows a proximal end of stylet 55 mounted in passageway 56 and surrounded by a hub 75. Preferably, hub 75 is supported by a plurality of longitudinal supports 70 extending radially frown hub 75. Each support 70 is separated from each other by 120 degrees and is attached to an inner wall 80 to securely hold and longitudinally position stylet 55 in lancet assembly 20. Stylet 55 is bonded in passageway 56 such that it extends from distal end 35 by a predetermined distance. FIG. 6 is a bottom plan view of lancet assembly 20 that more clearly shows an adhesive 85 surrounding stylet 55 in a reservoir 95 surrounded by an annular raised portion 90 for directing adhesive into passageway 56 when mounting stylet 55. Preferably, adhesive 85 is a ultraviolet (UV) cured adhesive, but other types of adhesive may be used with the present invention.

Figure 7:
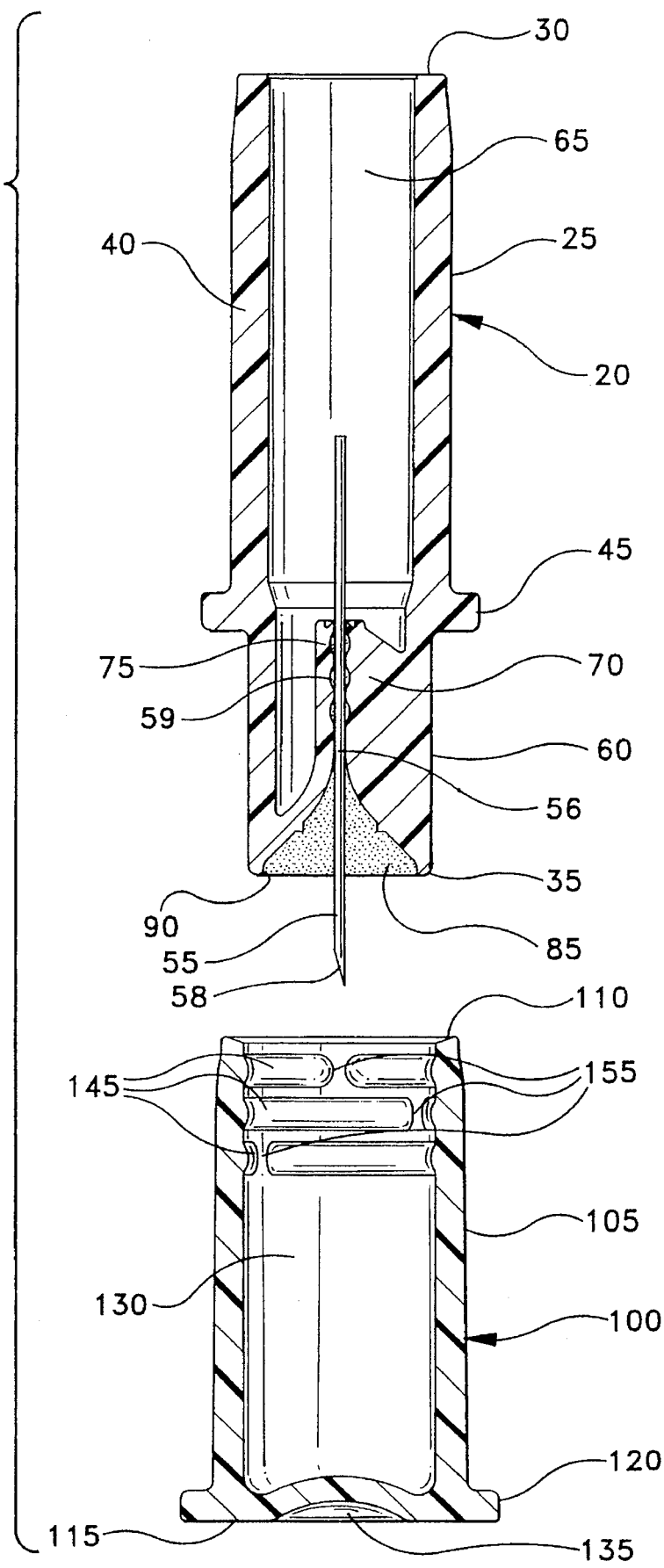
FIG. 7 is a cross-sectional view of the lancet assembly shown in FIG. 2, along line 7—7.

FIG. 7 is a cross-sectional view of lancet assembly 20 shown in FIG. 2, along line 7—7. As shown in FIG. 7, an upper chamber 65 extends from proximal top end 30 to a position level with flange 45 and just short of the entrance to passageway 56. Preferably, passageway 56 is shaped to receive stylet 55 and includes a wavy surface 59 to provide an enhanced surface for bonding stylet 55 in passageway 56. In addition, passageway 56 has an overall length sufficient to provide a straight stylet that is parallel to the longitudinal axis of housing 25. When cured, the adhesive forms a mechanical bond to the plastic passageway 56 and a chemical bond to the stainless steel stylet 55 having holding power greater than the force required to pierce a patient's skin when drawing a blood sample. FIG. 7 also more clearly shows the shape of supports 70 within lower annular portion 60 and labyrinth rings 145 within cap 100, each ring having gap 155 therein. The gap in each adjacent ring is preferably separated by 120 degrees to provide a labyrinth seal around stylet 55 when cap 100 is attached to lancet assembly 20.

As for manufacturing the lancet assemblies, housing 25 and cap 100 are injection molded from polypropylene and polyethylene, respectively. Applicants have found that using different materials in each part improves fit between the pans and makes it much easier to attach and remove cap 100 from housing 25. However, of course, these manufacturing techniques and materials are merely exemplary, various other manufacturing methods and materials could also be used.

In the foregoing discussion, it is to be understood that the above-described embodiments are simply illustrative of an improved lancet assembly, in accordance with the present invention. Other suitable variations and modifications could be made these embodiments and still remain within the scope of the present invention.

What is claimed is:

1. A lancet assembly comprising:

an annular housing having a proximal end and a distal bottom end connected by an outer wall with a passageway contained therein and a lower annular portion at said distal bottom end surrounding said passageway;

a stylet mounted in said passageway and extending a predetermined distance from said distal bottom end of said annular housing; and a cap for receiving said distal bottom end of said annular housing to shield said stylet when not in use, wherein said lower annular portion comprises a hub surrounding said passageway for holding and positioning said stylet in said annular housing and a plurality of supports extending radially from said hub to said outer wall to support said hub within said annular housing.

2. A lancet assembly according to claim 1, wherein said lower annular portion comprises a reservoir surrounding said passageway for directing liquid adhesive into said passageway after mounting said stylet in said passageway.

3. A lancet assembly according to claim 2, wherein said passageway includes an internal surface that directs the flow of liquid adhesive into said passageway from said reservoir when said stylet is being mounted in said passageway.

4. A lancet assembly according to claim 1, wherein each of said plurality of supports are separated by approximately 120 degrees.

5. A lancet assembly according to claim 1, wherein said annular housing is made of polypropylene and said cap is made of polyethylene to improve the fit between said annular housing and said cap and separation of said cap from said annular housing.

6. A lancet assembly according to claim 1, wherein said annular housing further comprises an annular flange to aid a user in removing said cap from said lancet assembly prior to use and in removing said lancet assembly from a blood sampling instrument after use.

7. A lancet assembly according to claim 6, wherein said cap includes a flange having an octagonal shape for positive grip and stability on a flat surface.

8. A lancet assembly according to claim 1, wherein said passageway includes an internal surface that directs the flow of liquid adhesive in said passageway when said stylet is being mounted in said passageway.

9. A lancet assembly according to claim 1, wherein said cap comprises:

a cylindrical housing having an open top end and a closed bottom end, said annular housing being received in said open top end when said lancet assembly is shielded; and a flange extending radially from said closed bottom end to aid a user in removing said cap from said annular housing and re-shielding said lancet assembly after use without holding said cap.

10. A lancet assembly according to claim 1, wherein said stylet is made of approximately 28 gauge stainless steel.

11. A lancet assembly comprising:

an annular housing having a proximal end and a distal bottom end connected by an outer wall with a passageway contained therein;

a stylet mounted in said passageway and extending a predetermined distance from said distal bottom end of said annular housing; and a cap for receiving said distal bottom end of said annular housing to shield said stylet when not in use, wherein said cap comprises:

a cylindrical housing having an open top end and a closed bottom end connected by an internal surface, said annular housing of said lancet assembly being received in said open top end when shielded; and a plurality of labyrinth rings extending from said internal surface of said cap that provide a labyrinth seal between said annular housing and said rings when said lancet assembly is shielded, wherein each labyrinth ring includes a gap offset from the other gaps.

12. A lancet assembly according to claim 11, wherein the offset between gaps in adjacent rings is approximately 120 degrees.

13. A lancet assembly according to claim 10, wherein said stylet is lubricated to reduce insertion force during use.

* * * * *

Disclaimer 5,569,286 - Allison A. Peckham, Pompton Plains, N.J.; Lennox O. Watts, Bronx; Marina Gertsek, Manhattan County, both of N.Y.; Kevin R. Smith, Holdrege, Nebraska; Don D. Taubenhaim, Holdrege, Nebraska; Ronald J. Pistulka, Holdrege, Nebraska. LANCET ASSEMBLY. Patent dated Oct. 29, 1996. Disclaimer filed Sept. 8, 1999, by the assignee, Becton Dickinson and Company.

Hereby enters this disclaimer to claim 1 of said patent.

*(Official Gazette, December 28, 1999)*